US00PP12532P2

(12) United States Plant Patent
Bergman

(10) Patent No.: US PP12,532 P2
(45) Date of Patent: Apr. 9, 2002

(54) CHRYSANTHEMUM PLANT NAMED 'SALMON YOSPRINGFIELD'

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/774,364

(22) Filed: Feb. 1, 2001

(51) Int. Cl.[7] ..... A01H 5/00
(52) U.S. Cl. ..... Plt./291

(58) Field of Search ..... Plt./291

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Chrysanthemum plant named 'Salmon Yospringfield', characterized by its uniform and upright plant habit; moderate vigor; dark green and glossy foliage; uniform flowering response; very early flowering, seven-week response time; large decorative-type inflorescences that are about 10.5 cm in diameter, soft salmon pink ray florets; and excellent postproduction longevity with plants maintaining good substance and color for about three weeks in an interior environment.

1 Drawing Sheet

BACKGROUND OF THE INVENTION

The present Invention relates to a new and distinct cultivar of Chrysanthemum plant, botanically known as *Chrysanthemum×morifolium* and hereinafter referred to by the name 'Salmon Yospringfield'.

The new Chrysanthemum is a product of a planned breeding program conducted by the Inventor in Fort Myers, Fla. The objective of the breeding program is to create new potted Chrysanthemum cultivars that are suitable for year-round production with uniform plant growth habit, desirable inflorescence form and floret colors, fast response time, and excellent postproduction longevity.

The new Chrysanthemum is a naturally-occurring whole plant mutation of a proprietary induced mutation that originated by exposing unrooted cuttings of the Chrysanthemum cultivar Yospringfield, disclosed in U.S. Plant Pat. No. 11,755, to X-ray radiation. The new Chrysanthemum was discovered and selected by the Inventor as a single flowering plant within a population of plants of the irradiated selection in April, 1998, in Fort Myers, Fla. The selection of this plant was based on its uniform plant growth habit, desirable inflorescence form and floret colors, fast response time, and excellent postproduction longevity. Plants of the new Chrysanthemum differ primarily from plants of the parent selection in ray floret color.

Asexual reproduction of the new Chrysanthemum by vegetative tip cuttings was first conducted in Fort Myers, Fla. in July, 1998. Asexual reproduction by cuttings has shown that the unique features of this new Chrysanthemum are stable and reproduced true to type in successive generations.

SUMMARY OF THE INVENTION

The cultivar Salmon Yospringfield has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Salmon Yospringfield'. These characteristics in combination distinguish 'Salmon Yospringfield' as a new and distinct Chrysanthemum:

1. Uniform and upright plant habit.
2. Moderate vigor.
3. Dark green and glossy foliage.
4. Uniform flowering response.
5. Typically grown as a disbud-type.
6. Very early flowering, seven-week response time.
7. Large decorative-type inflorescences that are about 10.5 cm in diameter.
8. Soft salmon pink ray florets.
9. Excellent postproduction longevity with plants maintaining good substance and color for about three weeks in an interior environment.

Plants of the new Chrysanthemum can be compared to plants of the cultivar Yospringfield. In side-by-side comparisons conducted by the Inventor in Salinas, Calif., plants of the new Chrysanthemum differ from plants of the cultivar Yospringfield in ray floret coloration and in the following characteristics:

1. Plants of the new Chrysanthemum are more vigorous and taller than plants of the cultivar Yospringfield.
2. Plants of the new Chrysanthemum have slightly larger inflorescence than plants of the cultivar Yospringfield.

Plants of the new Chrysanthemum can also be compared to plants of the Chrysanthemum cultivar Salmon Charm, disclosed in U.S. Plant Pat. No. 6,334. In side-by-side comparisons conducted by the Inventor in Salinas, Calf., plants of the new Chrysanthemum differ from plants of the cultivar Salmon Charm in the following characteristics:

1. Plants of the new Chrysanthemum are more compact and more outwardly spreading than plants of the cultivar Salmon Charm.
2. Plants of the new Chrysanthemum flower about one week earlier than plants of the cultivar Salmon Charm.
3. Plants of the new Chrysanthemum have larger inflorescences than plants of the cultivar Salmon Charm.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph at the top of the sheet comprises a top perspective view of a typical flowering plant of 'Salmon Yospringfield' grown a disbud-type.

The photograph at the bottom of the sheet comprises a close-up view of typical inflorescences of 'Salmon Yospringfield' grown as a disbud-type.

DETAILED BOTANICAL DESCRIPTION

In the following description, color references are made to The Royal Horticultural Society Colour Chart expect where general terms of ordinary dictionary significance are used. The following observations and measurements describe plants grown and flowered during the autumn in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 4,000 to 6,000 foot-candles. Four unrooted cuttings were directly stuck in 15-cm containers, exposed to long day/short night conditions, and pinched once about 14 days later. One week after the pinch, the photoinductive short day/long night treatments were started. Plants used for this description were grown as disbud-types. Measurements and numerical values represent averages of typical flowering plants.

Botanical classification: *Chrysanthemum×morifolium* cultivar Salmon Yospringfield.

Commercial classification: Decorative-type potted Chrysanthemum.

Parentage: Naturally-occurring whole plant mutation of a proprietary *Chrysanthemum×morifolium* induced mutation, U.S. Plant Pat. No. 11,755.

Propagation:

*Type.*—Terminal tip cuttings.

*Time to initiate roots.*—About four days at 21° C.

*Time to produce a rooted cutting.*—About ten days at 21° C.

*Root description.*—Fibrous and well-branched.

Plant description:

*Appearance.*—Herbaceous decorative-type potted Chrysanthemum typically grown as a disbud-type. Stems upright and outwardly spreading giving a uniformly flat-topped appearance to the plant. Freely branching, about three to four lateral branches develop after removal of terminal apex (pinching); dense and full plants. Moderate vigor. Relatively compact.

*Plant height.*—About 23 cm.

*Plant width.*—About 41 cm.

*Lateral branches.*—

Length: About 18 cm. Diameter: About 5 mm. Internode length: About 1.3 cm. Strength: Very strong. Texture: Pubescent. Color: 144A to 146A.

*Foliage description.*—Arrangement: Alternate. Quantity of leaves per lateral stem: About 14. Length: About 8.6 cm. Width: About 5.8 cm. Apex: Cuspidate. Base: Mostly truncate. Margin: Palmately lobed, sinuses between lateral lobes mostley divergent. Texture: Upper and lower surfaces with very fine pubescence; veins prominent on lower surface; leathery. Color: Young foliage, upper surface: Darker than 147A; glossy. Young foliage, lower surface: Darker than 147B. Mature foliage, upper surface: Darker than 147A; glossy. Mature foliage, lower surface: Darker than 147B. Venation, upper surface: 147A to 147B. Venation, lower surface: 147B. Petiole length: About 2.2 cm. Petiole diameter: About 2.5 mm. Petiole color: 147B.

Inflorescence description:

*Appearance.*—Decorative-type inflorescence form with elongated oblong-shaped ray florets. Inflorescences borne on terminals above foliage. Disk and ray florets arranged acropetally on a capitulum. Not fragrant. Typically grown as a disbud-type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to three weeks of long day/short night conditions followed by photoinductive short day/long night conditions flower about 45 days later when grown during the summer and flower about 50 days later when grown during the winter.

*Postproduction longevity.*—Inflorescences maintain good color and substance for about three weeks in an interior environment.

*Quantity of Inflorescences.*—Produced as a disbud-type, all the lateral inflorescences are removed leaving only the terminal inflorescence.

*Inflorescence bud.*—Height: About 7.5 mm. Diameter: About 1 cm. Color: Darker than 143A.

*Inflorescence size.*—Diameter: Large, about 10.5 cm. Depth (height): About 3.2 cm. Diameter of disc: About 6.2 mm, inconspicious. Receptacle diameter: About 1 cm.

*Ray florets.*—Shape: Elongated-oblong. Orientation: Initially upright, then about 90° from vertical or perpendicular to the peduncle, eventually reflexed. Aspect: Initially incurved, then convex. Length: About 5.7 cm. Width: About 1 cm. Corolla tube length: About 4 mm. Apex: Emarginate or acute. Base: Attenuate; short corolla tube. Margin: Entire. Texture: Smooth, glabrous, satiny. Number of ray florets per inflorescence: Numerous, about 272. Color: When opening, both surfaces: 9C overlain with 59A; overall tonality, close to 186A. Fully opened, upper surface: 9D overlain with 59A; overall tonality, close to 35B to 35C; color fading to close to 35C to 35D with subsequent development. Fully opened, lower surface: 10D underlain with 59A; overall tonality, close to 38C.

*Disc florets.*—Arrangement: Massed at center of receptacle, inconspicuous. Shape: Tubular, elongated. Apex: Five-pointed. Length: About 5 mm. Width: Apex, about 1.5 mm; base, about 1 mm. Number of disc florets per inflorescence: About 22. Color: Immature: 144A to 154A. Mature: Apex: 12A. Mid-section: Close to 145D. Base: 155D.

*Reproductive organs.*—Androecium: Present on disc florets only. Anther color: 12A. Pollen amount:

None. Gynoecium: Present on both ray and disc florets.

*Seed.*—Seed production has not been observed.

Disease resistance: Resistance to pathogens common to Chrysanthemums has not been observed on plants grown under commercial greenhouse conditions.

It is claimed:

1. A new and distinct cultivar of Chrysanthemum plant named 'Salmon Yospringfield', as illustrated and described.

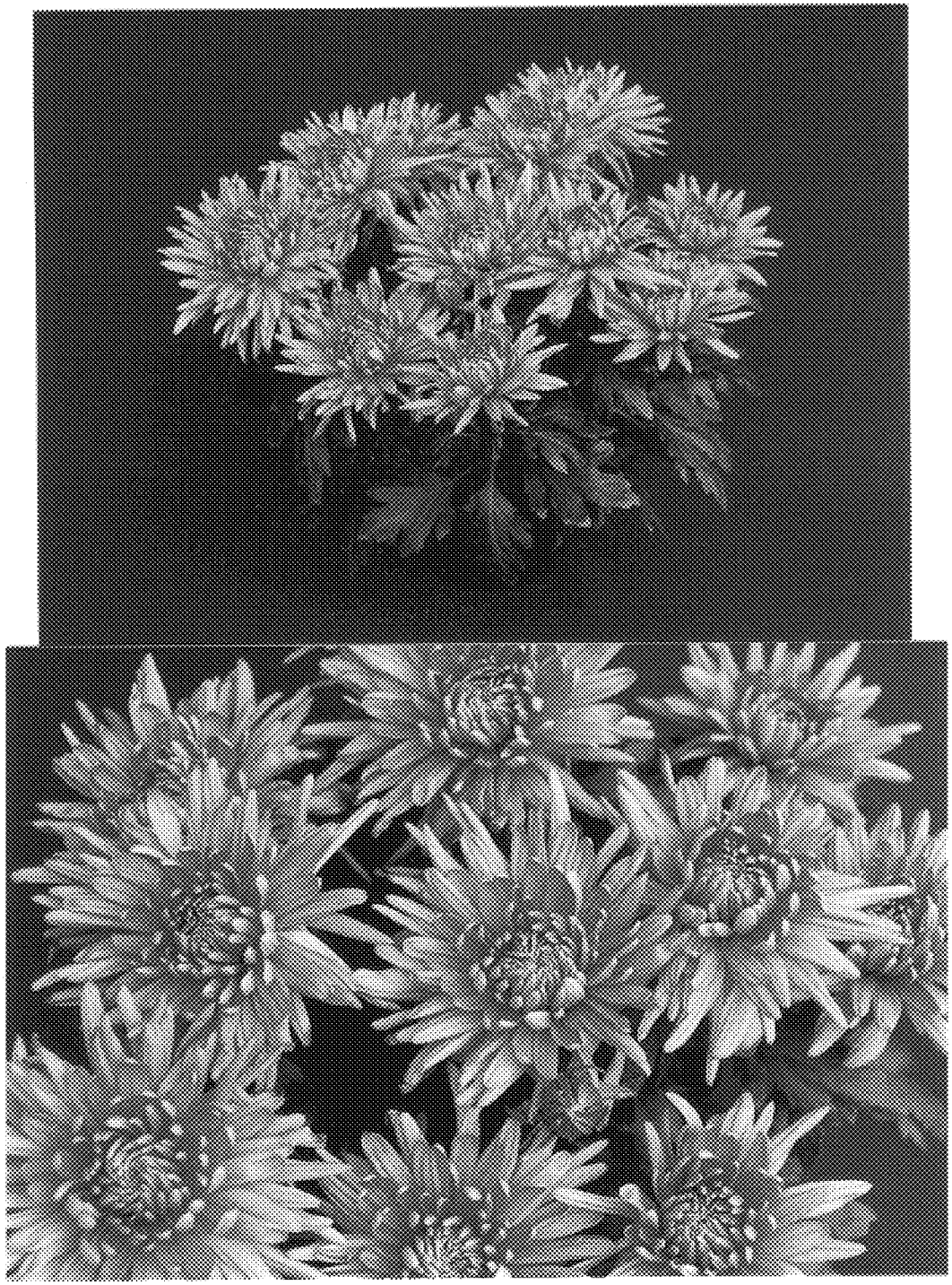

* * * * *